United States Patent
Segawa et al.

(10) Patent No.: US 11,377,405 B2
(45) Date of Patent: Jul. 5, 2022

(54) INDENE COMPOSITION

(71) Applicant: ENEOS Corporation, Tokyo (JP)

(72) Inventors: Atsushi Segawa, Tokyo (JP); Yasuyuki Iwasa, Tokyo (JP); Kazuya Mayumi, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 17/281,435

(22) PCT Filed: Nov. 21, 2019

(86) PCT No.: PCT/JP2019/045676
§ 371 (c)(1),
(2) Date: Mar. 30, 2021

(87) PCT Pub. No.: WO2020/105711
PCT Pub. Date: May 28, 2020

(65) Prior Publication Data
US 2021/0395172 A1 Dec. 23, 2021

(30) Foreign Application Priority Data
Nov. 22, 2018 (JP) .............................. JP2018-219499

(51) Int. Cl.
| | | |
|---|---|---|
| *C07C 13/465* | (2006.01) | |
| *C07C 5/333* | (2006.01) | |
| *C07C 5/367* | (2006.01) | |
| *C07C 7/04* | (2006.01) | |

(52) U.S. Cl.
CPC .......... *C07C 13/465* (2013.01); *C07C 5/3337* (2013.01); *C07C 5/367* (2013.01); *C07C 7/04* (2013.01); *C07C 2602/08* (2017.05)

(58) Field of Classification Search
CPC ..... C07C 13/465; C07C 5/3337; C07C 5/367; C07C 7/04; C07C 2602/08
See application file for complete search history.

(56) References Cited

U.S. PATENT DOCUMENTS 6,380,450 B1   4/2002  Yasuo

FOREIGN PATENT DOCUMENTS

| JP | 09-301898    | 11/1997 |
| JP | 2000-063298  | 2/2000  |
| JP | 2000-063299  | 2/2000  |
| JP | 2001-072613  | 3/2001  |
| JP | 2013-133293  | 7/2013  |

OTHER PUBLICATIONS

ISR issued in International Patent Application No. PCT/JP2019/045676, dated Feb. 18, 2020, English translation.
Written Opinion of International Searching Authority issued in International Patent Application No. PCT/JP2019/045676, dated Feb. 18, 2020, English translation.
IPRP issued in International Patent Application No. PCT/JP2019/045676, dated May 25, 2021, English translation.

*Primary Examiner* — Thuan D Dang
(74) *Attorney, Agent, or Firm* — Greenblum & Bernstein, P.L.C.

(57) ABSTRACT

The present invention provides an indene composition having a content of indene of 80 to 99.5% by mass, in which a content ratio of a hydrocarbon compound having a condensed ring structure of a 5-membered ring and a 6-membered ring, and having 9 or 10 carbon atoms, in a component contained in addition to indene, is 90% by mass or more, and a content of benzonitrile is 0.5% by mass or less, and a content of sulfur is 5 ppm by mass or less.

3 Claims, No Drawings

INDENE COMPOSITION

TECHNICAL FIELD

The present invention relates to an indene composition comprising indene as a principal component.

BACKGROUND ART

Indene is an industrially useful substance as a material of a coumarone-indene resin or an optical resin. As a method for producing indene, a method for collecting indene from a coal tar distillate is generally conventionally employed. For example, Patent Literatures 1 and 2 describe methods for producing indene with high impurity from a coal tar distillate.

CITATION LIST

Patent Literature

Patent Literature 1: Japanese Unexamined Patent Publication No. 9-301898
Patent Literature 2: Japanese Unexamined Patent Publication No. 2001-72613

SUMMARY OF INVENTION

Technical Problem

When obtained by the methods described in Patent Literatures 1 and 2, however, indene itself is colored, or difficult to be used as a synthesis raw material in some cases due to influence of benzonitrile, a sulfur content or the like remaining therein in a slight amount.

An object of the present invention is to provide an indene composition less colored, and suitably usable as a synthesis raw material of a polymer or the like.

Solution to Problem

The present invention relates to an indene composition having a content of indene of 80 to 99.5% by mass. In the indene composition, a content ratio of a hydrocarbon compound having a condensed ring structure of a 5-membered ring and a 6-membered ring, and having 9 or 10 carbon atoms, in a component contained in addition to indene, is 90% by mass or more. Besides, in the indene composition, a content of benzonitrile is 0.5% by mass or less, and a content of sulfur is 5 ppm by mass or less.

The component contained in addition to indene is mostly a specific hydrocarbon compound, and the contents of benzonitrile and sulfur having high reactivity are small, and hence, the indene composition is less colored, and can be suitably used as a synthesis raw material of a polymer, a pharmaceutical compound or the like.

In one aspect, the hydrocarbon compound may contain an alicyclic compound having 9 or 10 carbon atoms.

In another aspect, the alicyclic compound may contain a compound having a condensed ring structure in which a cyclohexene ring and a cyclopentene ring are condensed with each other, and having 9 carbon atoms.

In another aspect, the alicyclic compound may contain a compound having a condensed ring structure in which a norbornane ring or a norbornene ring and a 5-membered ring are condensed with each other, and having 10 carbon atoms.

In one aspect, a content of the alicyclic compound may be 0.1 to 1% by mass.

In one aspect, the hydrocarbon compound may contain at least one aromatic compound selected from the group consisting of indane, methylindane, and methylindene.

In one aspect, a content of the aromatic compound may be 0.1 to 19.9% by mass.

Advantageous Effects of Invention

According to the present invention, an indene composition little colored, and suitably usable as a synthesis raw material of a polymer or the like is provided.

DESCRIPTION OF EMBODIMENTS

A preferable embodiment of the present invention will now be described in detail.

An indene composition according to the present embodiment is a composition containing indene as a principal component (80 to 99.5% by mass), and contains, as a component contained in addition to indene, a hydrocarbon compound having a condensed ring structure of a 5-membered ring and a 6-membered ring, and having 9 or 10 carbon atoms.

A content ratio of the hydrocarbon compound, in the component contained in addition to indene, is 90% by mass or more, and preferably 95% by mass or more. The hydrocarbon compound does not have a polar functional group containing a hetero atom, and hence is difficult to cause coloring, and is difficult to cause synthesis inhibition due to an unexpected reaction. Besides, the hydrocarbon compound has a condensed ring structure similar to that of indene, and hence tends to cause little harmful effects even if involved in an unexpected reaction.

A content of benzonitrile in the indene composition is 0.5% by mass or less, preferably 0.1% by mass or less, and more preferably 0.05% by mass or less, and may be 0% by mass (no benzonitrile is contained). Since benzonitrile has a cyano group having high reactivity, it causes coloring when contained in a large content, and can easily cause an unexpected reaction or catalyst degradation. In conventional indene derived from a coal tar distillate, since benzonitrile has a boiling point near to that of indene, the content of benzonitrile cannot be reduced to the above-described range, and hence, it is difficult to suppress coloring and the like. Since the content of benzonitrile in the indene composition of the present embodiment is reduced to 0.5% by mass or less owing to a production method and the like described later, a problem of coloring and the like is remarkably suppressed.

A content of sulfur (sulfur content) in the indene composition is 5 ppm by mass or less, preferably 3 ppm by mass or less, and more preferably 1 ppm by mass or less, and may be 0% by mass (no sulfur is contained). Herein, the content of sulfur in the indene composition indicates a content in terms of a sulfur atom (what is called a sulfur content), and is a value obtained through measurement by an ultraviolet fluorescence method.

In the present embodiment, examples of the hydrocarbon compound having a condensed ring structure of a 5-membered ring and a 6-membered ring, and having 9 or 10 carbon atoms include an alicyclic compound and an aromatic compound.

An alicyclic compound has a condensed ring structure in which an alicyclic 5-membered ring and an alicyclic 6-membered ring are condensed with each other. In an alicyclic compound having 10 carbon atoms, a methyl group may be substituted in the 5-membered ring or the 6-membered ring, or the 6-membered ring may have a bicyclic structure in which a methylene group is crosslinked in the 1,4-position (such as a norbornane ring or a norbornene ring).

The alicyclic compound preferably has a boiling point close to that of indene from the viewpoint that it can be easily contained in the indene composition by the production method described later. The boiling point of indene is 182° C., and the boiling point of the alicyclic compound is preferably 160 to 200° C.

An example of the alicyclic compound includes a compound having a condensed ring structure in which a cyclohexene ring and a cyclopentene ring are condensed with each other, and having 9 carbon atoms. An example of such a compound includes a compound represented by the following formula (1-1) (bicyclo(4,3,0)-2,9-nonadiene).

[Chemical Formula 1]

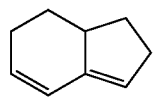

(1-1)

From the viewpoint that synthesis inhibition due to an unexpected reaction is more difficult to occur, the alicyclic compound is suitably a compound having a rigid condensed ring structure including a norbornane ring or a norbornene ring (namely, a compound having a condensed ring structure in which a norbornane ring or a norbornene ring and a 5-membered ring are condensed with each other, and having 10 carbon atoms). Examples of such an alicyclic compound include a compound represented by the following formula (2-1) (hexahydro-4,7-methanoindene), and a compound represented by the following formula (2-2) (octahydro-4,7-methanoindene).

[Chemical Formula 2]

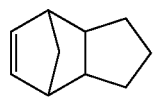

(2-1)

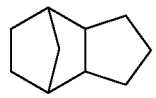

(2-2)

A content of the alicyclic compound in the indene composition may be, for example, 0.1% by mass or more, and may be 0.5% by mass or more. Besides, the content of the alicyclic compound in the indene composition may be, for example, 1.0% by mass or less, and may be 0.8% by mass or less.

An aromatic compound has a condensed ring structure in which a benzene ring (6-membered ring) and a 5-membered ring are condensed with each other. Examples of the aromatic compound include indane, methylindane, and methylindene. In an aromatic compound having 10 carbon atoms, a methyl group may be substituted in the 5-membered ring or the 6-membered ring.

The aromatic compound preferably has a boiling point close to that of indene from the viewpoint that it can be easily contained in the indene composition by the production method described later. The boiling point of indene is 182° C., and the boiling point of the aromatic compound is preferably 140 to 220° C.

A content of the aromatic compound in the indene composition may be, for example, 0.1% by mass or more, and may be 1.0% by mass or more. Besides, the content of the aromatic compound in the indene composition may be, for example, 19.9% by mass or less, and may be 10.0% by mass or less.

A method for producing the indene composition of the present embodiment is not especially limited, and the indene composition can be easily produced by, for example, a production method A or a production method B described below.

(Production Method A for Indene Composition)

The production method A comprises a dehydrogenation step of obtaining a reaction product containing indene by contacting a raw material composition containing indane with a dehydrogenation catalyst; and a purification step of obtaining the above-mentioned indene composition by purifying the reaction product. In this production method, the dehydrogenation catalyst comprises a support containing aluminum, and a group 14 metal element and platinum supported on the support, a content of the platinum in the dehydrogenation catalyst is 0.6 to 4.0% by mass based on the whole amount of the dehydrogenation catalyst, and an atomic ratio of the group 14 metal element to the platinum in the dehydrogenation catalyst is 4.0 to 20.0.

In this production method, a hydrocarbon compound having a boiling point close to that of indene, having a condensed ring structure of a 5-membered ring and a 6-membered ring, and having 9 or 10 carbon atoms is generated as a by-product of the reaction (namely, the reaction product contains the hydrocarbon compound). Therefore, when the reaction product obtained by the above-described production method is treated by an ordinary purification method such as distillation, the above-mentioned indene composition can be easily obtained.

The dehydrogenation catalyst used in the production method A is a catalyst comprising a support containing aluminum, and a group 14 metal element and platinum supported on the support. Here, a group 14 metal element means a metal element belonging to the group 14 of the long-form periodic table of elements based on the definition of IUPAC (International Union of Pure and Applied Chemistry). Examples of the group 14 metal element include tin (Sn) and lead (Pb).

A method for preparing the dehydrogenation catalyst is not especially limited, and may be a method in which the group 14 metal element is caused to be supported on the support, and then platinum is further caused to be supported thereon, a method in which platinum is caused to be supported on the support, and then the group 14 metal element is further caused to be supported thereon, or a method in which the group 14 metal element and platinum are simultaneously caused to be supported on the support.

In the dehydrogenation catalyst, each of the support containing aluminum, the group 14 metal element and platinum may be present in the form of an oxide, may be present in the form of a complex oxide with another metal, or may be present in the form of a metal salt or a metal simple substance.

The dehydrogenation catalyst may comprise another metal element in addition to aluminum, the group 14 metal element and platinum. Examples of another metal element include lithium (Li), sodium (Na), potassium (K), magnesium (Mg), calcium (Ca), zin (Zn), iron (Fe), indium (In), selenium (Se), antimony (Sb), nickel (Ni), and gallium (Ga).

In one aspect, the dehydrogenation catalyst may be a catalyst in which a supported metal including the group 14 metal element and platinum is supported on the support containing aluminum. In another aspect, the dehydrogenation catalyst may be a catalyst in which a supported metal including platinum is supported on a support containing aluminum and the group 14 metal element.

The support is preferably an inorganic oxide support containing aluminum. An inorganic oxide containing aluminum may be an oxide singly containing aluminum as a metal, or may be a complex oxide of aluminum with another metal. The oxide singly containing aluminum as a metal may be, for example, alumina ($Al_2O_3$). The complex oxide of aluminum and another metal may be, for example, a complex oxide of aluminum and magnesium (Mg), a complex oxide of aluminum and tin (Sn), a complex oxide of aluminum and lead (Pb), or a complex oxide of aluminum, and zinc (Zn), selenium (Se), iron (Fe), indium (In) or the like.

An example of the inorganic oxide support containing aluminum includes a support containing an inorganic oxide such as alumina, alumina magnesia, silica alumina, zirconia alumina, or a spinel structure (magnesium spinel).

A content of aluminum in the support may be 25% by mass or more, and is preferably 50% by mass or more based on the whole amount of the support.

A specific surface area of the support may be, for example, 30 $m^2/g$ or more, and is preferably 50 $m^2/g$ or more. Thus, the effect of increasing the conversion rate of indane can be exhibited. The specific surface area of the support may be, for example, 1000 $m^2/g$ or less, and is preferably 500 $m^2/g$ or less. Thus, a support having sufficient strength to be suitably industrially applicable can be obtained. It is noted that the specific surface area of the support is herein measured with a BET specific surface area meter employing a nitrogen adsorption method.

A method for preparing the support is not especially limited, and examples include a sol-gel method, a coprecipitation method, and a hydrothermal method.

A content of platinum in the dehydrogenation catalyst is 0.6 to 4.0% by mass based on the whole amount of the dehydrogenation catalyst. An amount of platinum supported is preferably 0.7% by mass or more based on the whole amount of the dehydrogenation catalyst. The amount of platinum supported is preferably 3.5% by mass or less based on the whole amount of the dehydrogenation catalyst. When such an amount supported is employed, a platinum particle to be formed on the catalyst can be easily made to have a size suitable for the dehydrogenation reaction, and a platinum surface area per unit platinum weight is increased, and therefore, a more efficient reaction system can be realized.

An atomic ratio of the group 14 metal element to platinum in the dehydrogenation catalyst is 4.0 to 20.0, and preferably 7.0 to 20.0. The ratio is more preferably 18.0 or less. When the ratio falls in the aforementioned range, a side reaction is more remarkably inhibited, and in addition, the conversion rate of indane tends to be further improved.

A content of the group 14 metal element in the dehydrogenation catalyst is not especially limited, and may be appropriately changed, for example, in a range satisfying the above-mentioned ratio. An amount of the group 14 metal element supported is, for example, 1.5% by mass or more, and preferably 2.5% by mass or more based on the whole amount of the dehydrogenation catalyst. The amount of the group 14 metal element supported is, for example, 25% by mass or less, and preferably 15% by mass or less based on the whole amount of the dehydrogenation catalyst.

The group 14 metal element may be, for example, at least one selected from the group consisting of germanium (Ge), tin (Sn), and lead (Pb). Among these, when the group 14 metal element is tin, the effects of the present invention are further remarkably exhibited.

The dehydrogenation catalyst may be one obtained by causing platinum and tin to be supported on the support by using a platinum source and a tin source. Examples of the platinum source include tetraammineplatinous(II) acid, tetraammineplatinum(II) acid salt (such as nitrate), a tetraammineplatinous(I) hydroxide solution, a dinitrodiammineplatinous(II) nitric acid solution, a hexahydroxoplatinic(IV) nitric acid solution, and a hexahydroxoplatinic(IV) ethanolamine solution. Examples of the tin source include sodium stannate and potassium stannate. As each of the platinum source and the tine source, a metal source not containing a chlorine atom is preferably used. When a metal source not containing a chlorine atom is used, corrosion of an apparatus used can be inhibited, and indane can be more efficiently dehydrogenated.

A supporting method for a supported metal is not especially limited, and examples include an impregnation method, a deposition method, a coprecipitation method, a kneading method, an ion exchange method, and a pore filling method.

One aspect of the supporting method will now be described. First, a support is added to a solution containing precursors (a group 14 metal element source and a platinum source) of supported metals, and the resultant support containing the solution is kneaded. Thereafter, a solvent is removed by drying, the thus obtained solid is baked, and thus, the supported metals can be supported on the support.

Baking can be performed, for example, in an air atmosphere or in an oxygen atmosphere. The baking may be performed in single stage, or in multiple stages of two or more stages. A baking temperature may be a temperature at which the precursors of the supported metals can be decomposed, and for example, may be 200 to 1000° C., or may be 400 to 800° C. Incidentally, when the baking is performed in multiple stages, the baking temperature may be employed in at least one of the stages. Baking temperatures employed in the other stages may be, for example, in the same range as described above, or may be 100 to 200° C.

The dehydrogenation catalyst may be molded by a method such as an extruding method or a tableting method.

From the viewpoint of improvement of moldability, the dehydrogenation catalyst may further contain a molding aid as long as the physical properties and catalytic performance of the catalyst are not impaired. The molding aid may be, for example, at least one selected from the group consisting of a thickener, a surfactant, a water retention agent, a plasticizer, and a binder material. A molding step of molding the dehydrogenation catalyst may be performed at a suitable stage in the production process of the dehydrogenation catalyst in consideration of the reactivity of the molding aid.

A shape of the dehydrogenation catalyst is not especially limited, and can be appropriately selected in accordance with a form in which the catalyst is used. The shape of the dehydrogenation catalyst may be, for example, a pellet shape, a granular shape, a honeycomb shape, or a sponge shape.

The dehydrogenation catalyst may be subjected, before use, to a reduction treatment as a pretreatment. The reduction treatment can be performed, for example, by holding the dehydrogenation catalyst in a reducing gas atmosphere at 40 to 600° C. A holding time may be, for example, 0.05 to 24 hours. The reducing gas may contain, for example, hydrogen or carbon monoxide. When the dehydrogenation catalyst having been subjected to the reduction treatment is used, an initial induction period of the dehydrogenation reaction can be shortened. The initial induction period of the dehydrogenation reaction refers to a state where a very small amount of a supported metal contained in a dehydrogenation catalyst has been reduced to be placed in an active state such that the activity of the catalyst is low.

Next, the dehydrogenation step of the production method A will be described in detail.

In the production method A, the raw material composition containing indane is contacted with the dehydrogenation catalyst in the dehydrogenation step. Thus, indane is dehydrogenated to obtain a reaction product containing indene.

The raw material composition may further contain another component in addition to indane. For example, the raw material composition may further contain an inert gas such as nitrogen or argon, steam, hydrogen, oxygen, carbon monoxide, a carbon dioxide gas, an alkane, an olefin, or the like.

When the raw material composition contains another component in addition to indane, a mole fraction of indane in the raw material composition is preferably 0.1 or more, and more preferably 0.2 or more. An upper limit of the mole fraction of indane in the raw material composition is not especially limited, and may be, for example, 0.95 or less, and is preferably 0.9 or less. When another component is contained in addition to indane, the dehydrogenation reaction tends to easily proceed to inhibit activity degradation of the catalyst. But a large amount of energy is necessary for heating this component, and hence the amount of the component needs to be adequate from an industrial viewpoint. When the mole fraction of indane in the raw material composition falls in the above-described range, energy necessary for the dehydrogenation reaction is further restrained, and hence indane can be efficiently dehydrogenated.

The dehydrogenation step may be performed, for example, by using a reactor filled with the dehydrogenation catalyst, and by causing the raw material composition to pass through the reactor. As the reactor, any of various reactors used for a gas phase reaction using a solid catalyst can be used. Examples of the reactor include a fixed bed adiabatic reactor, a radial flow reactor, and a tubular reactor.

A reaction method for the dehydrogenation may be, for example, a fixed bed method, a moving bed method, or a fluidized bed method. Among these, the fixed bed method is preferred from the viewpoint of equipment cost.

A temperature at which the raw material composition is contacted with the dehydrogenation catalyst is a reaction temperature of the dehydrogenation, and can be said as a temperature within the reactor. From the viewpoint of reaction efficiency, the reaction temperature of the dehydrogenation may be 350 to 800° C., may be 400 to 700° C., or may be 450° C. to 650° C. When the reaction temperature of the dehydrogenation reaction is 350° C. or more, the yield of indene tends to be further improved because equilibrium conversion of indane is not too low. When the reaction temperature of the dehydrogenation reaction is 800° C. or less, the dehydrogenation catalyst tends to retain its high activity for a longer period of time because a coking rate is not too high.

A pressure at which the raw material composition is contacted with the dehydrogenation catalyst, namely, an atmospheric pressure within the reactor, may be 0.01 to 4.0 MPa, may be 0.03 to 0.5 MPa, or may be 0.01 to 0.3 MPa. When the reaction pressure falls in the above-described range, the dehydrogenation reaction tends to easily proceed to obtain further excellent reaction efficiency.

When the dehydrogenation step is performed by a continuous reaction method for continuously supplying the raw material, a liquid hourly space velocity (hereinafter referred to as the "LHSV") may be 0.01 $h^{-1}$ or more, or may be 0.1 $h^{-1}$ or more. When such an LHSV is employed, the conversion rate of indane can be further increased. The LHSV may be 100 $h^{-1}$ or less, or may be 20 $h^{-1}$ or less. When the LHSV falls in the above-described range, the reactor size can be further reduced. Here, the LHSV refers to a ratio (F/L) of a supply rate (amount supplied/time) F of the raw material to the volume L of the dehydrogenation catalyst in a continuous reaction device. It is noted that further preferable ranges of amounts of the raw material and the catalyst used may be appropriately selected in accordance with reaction conditions, the activity of the catalyst and the like, and the LHSV is not limited to the above-described range.

The production method A may further include the raw material synthesis step of obtaining indane by dehydrogenation reaction of tetrahydroindene. In such a production method, the reactor may be further filled with a catalyst other than the dehydrogenation catalyst (hereinafter sometimes referred to as the "second dehydrogenation catalyst").

For example, in the production method A, an upstream stage of the second dehydrogenation catalyst in the reactor may be further filled with a solid catalyst (hereinafter sometimes referred to as the "first dehydrogenation catalyst") catalyzing the dehydrogenation reaction from tetrahydroindene to indane. Since the second dehydrogenation catalyst is excellent particularly in the reaction activity of the dehydrogenation reaction from indane to indene, when the upstream stage of the second dehydrogenation catalyst is filled with the first dehydrogenation catalyst, indene can be more efficiently produced from tetrahydroindene.

As the first dehydrogenation catalyst, any one of catalysts for dehydrogenation reaction of tetrahydroindene can be used without any limitation. As the first dehydrogenation catalyst, for example, a chromium/$Al_2O_3$ catalyst, a platinum/$Al_2O_3$ catalyst and a Fe—K catalyst, which are used as catalysts for dehydrogenation reaction, or a Bi—Mo catalyst usually used as a catalyst for oxidative dehydrogenation reaction can be used.

In the production method A, the purification method employed in the purification step is not especially limited, and any method can be employed as long as the indene composition can be obtained.

The purification step is preferably a step of obtaining the indene composition by distillation purification of the reaction product. According to the production method A, since a hydrocarbon compound having a boiling point close to that of indene, having a condensed ring structure of a 5-membered ring and a 6-membered ring, and having 9 or 10 carbon atoms is generated as a by-product of the reaction, the above-mentioned indene composition can be easily obtained by distillation purification of the reaction product.

(Production Method B for Indene Composition)

The production method B comprises a dehydrogenation step of obtaining a reaction product containing indene by contacting a raw material gas containing indane and molecular hydrogen with a dehydrogenation catalyst; and a purification step of obtaining the above-mentioned indene composition by purifying the reaction product. In this production method, the dehydrogenation catalyst comprises a support containing aluminum, and a supported metal supported on the support, the supported metal contains a group 14 metal element and platinum, and an atomic ratio of the group 14 metal element to the platinum in the dehydrogenation catalyst is 8.0 or less.

In this production method, a hydrocarbon compound having a boiling point close to that of indene, having a condensed ring structure of a 5-membered ring and a 6-membered ring, and having 9 or 10 carbon atoms is generated as a by-product of the reaction (namely, the reaction product contains the hydrocarbon compound). Therefore, when the reaction product obtained by the above-described production method is treated by an ordinary purification method such as distillation, the above-mentioned indene composition can be easily obtained.

The dehydrogenation catalyst used in the production method B is a catalyst comprising the support containing aluminum, and the supported metal supported on the support. The supported metal contains a group 14 metal element and platinum. Here, a group 14 metal element means a metal element belonging to the group 14 of the long-form periodic table of elements based on the definition of IUPAC (International Union of Pure and Applied Chemistry). Examples of the group 14 metal element include tin (Sn) and lead (Pb).

A method for preparing the dehydrogenation catalyst is not especially limited, and may be a method in which the group 14 metal element is caused to be supported on the support, and then platinum is further caused to be supported thereon, may be a method in which platinum is caused to be supported on the support, and then the group 14 metal element is further caused to be supported thereon, or may be a method in which the group 14 metal element and platinum are simultaneously caused to be supported on the support.

The support is preferably an inorganic oxide support containing aluminum. The support may be a support containing alumina ($Al_2O_3$), or may be a support containing a complex oxide of Al with another metal. More specifically, a metal oxide support may be a support containing a metal oxide, such as alumina, a complex oxide of Al and Mg, a complex oxide of Al and Sn, a complex oxide of Al and Pb, or a complex oxide of Al and Zn, Se, Fe, or In. A content of Al in the support may be 25% by mass or more, and is preferably 50% by mass or more based on the whole amount of the support. An example of the inorganic oxide support containing Al includes a support containing an inorganic oxide, such as alumina, alumina magnesia, silica alumina, zirconia alumina, or a spinel structure (magnesium spinel).

A method for preparing the support is not especially limited, and examples include a sol-gel method, a coprecipitation method, and a hydrothermal method.

A specific surface area of the support may be, for example, 30 $m^2/g$ or more, and is preferably 50 $m^2/g$ or more. Thus, the conversion rate of indane tends to be further improved. The specific surface area of the support may be, for example, 1000 $m^2/g$ or less, and is preferably 500 $m^2/g$ or less. When the support has such a specific surface area, the support can attain sufficient strength suitably industrially applicable. It is noted that the specific surface area of the support is herein measured with a BET specific surface area meter employing a nitrogen adsorption method.

In the dehydrogenation catalyst, each of the supported metals including the group 14 metal element and platinum may be present in the form of a single oxide, may be present in the form of a complex oxide with another metal, or may be present in the form of a metal salt or a metal simple substance.

The dehydrogenation catalyst may be one obtained by causing the supported metal to be supported on the support by using a metal source (a compound containing the supported metal).

Examples of a platinum source include tetraammineplatinous(II) acid, tetraammineplatinum(II) acid salt (such as nitrate), a tetraammineplatinous(II) hydroxide solution, a dinitrodiammineplatinous(II) nitric acid solution, a hexahydroxoplatinic(IV) nitric acid solution, and a hexahydroxoplatinic(IV) ethanolamine solution. The platinum source is preferably a compound containing platinum (platinum) but not containing a chlorine atom.

An amount of platinum supported is 0.1% by mass or more, and preferably 0.5% by mass or more based on the whole amount of the dehydrogenation catalyst. The amount of platinum supported is 5.0% by mass or less, and preferably 3.0% by mass or less based on the whole amount of the dehydrogenation catalyst. When such an amount supported is employed, a platinum particle to be formed on the catalyst can be easily made to have a size suitable for the dehydrogenation reaction, and a platinum surface area per unit platinum weight is increased, and therefore, a more efficient reaction system can be realized.

An example of the group 14 metal elements include tin. Examples of a tin source include sodium stannate and potassium stannate. The tin source is preferably a compound containing tin (Sn) but not containing a chlorine atom.

In the dehydrogenation catalyst, an atomic ratio (M/Pt) of the group 14 metal element (M) to platinum (Pt) is 8.0 or less, preferably 6.5 or less, and more preferably 5.0 or less. The atomic ratio (M/Pt) of the group 14 metal element (M) to platinum (Pt) is preferably 1.0 or more, and more preferably 3.5 or more. When the atomic ratio falls in the above-described range, the yield of indene tends to be further improved.

The dehydrogenation catalyst may further comprise another metal element in addition to the group 14 metal element and platinum. Examples of another metal element include lithium (Li), sodium (Na), potassium (K), magnesium (Mg), calcium (Ca), zinc (Zn), iron (Fe), indium (In), selenium (Se), antimony (Sb), nickel (Ni), and gallium (Ga).

A supporting method for a supported metal is not especially limited, and examples include an impregnation method, a deposition method, a coprecipitation method, a kneading method, an ion exchange method, and a pore filling method.

One aspect of the supporting method will now be described. First, a support is added to a solution containing a precursor (a metal source) of a supported metal, and the resultant support containing the solution is kneaded. Thereafter, a solvent is removed by drying, the thus obtained solid is baked, and thus, the supported metal can be supported on the support.

The precursor of the supported metal is preferably a metal source not containing a chlorine atom. When a metal source not containing a chlorine atom is used as the precursor, corrosion of an apparatus used for the adjustment of the catalyst can be prevented.

Baking can be performed, for example, in an air atmosphere or in an oxygen atmosphere. The baking may be performed in a single stage, or in multiple stages of two or more stages. A baking temperature may be a temperature at which the precursor of the supported metal can be decomposed, and for example, may be 200 to 1000° C., or may be 400 to 800° C. Incidentally, when the baking is performed in multiple stages, the baking temperature may be employed in at least one of the stages. Baking temperatures employed in the other stages may be, for example, in the same range as described above, or may be 100 to 200° C.

From the viewpoint of improvement of moldability, the dehydrogenation catalyst may further contain a molding aid. The molding aid may be, for example, a thickener, a surfactant, a water retention agent, a plasticizer, or a binder material.

A shape of the dehydrogenation catalyst is not especially limited, and may be, for example, a pellet shape, a granular shape, a honeycomb shape, or a sponge shape. The dehydrogenation catalyst may be molded by a method such as an extruding method or a tableting method.

Next, the dehydrogenation step of the production method B will be described in detail.

The dehydrogenation step is a step of obtaining a reaction product containing indene by contacting a raw material gas containing indane and molecular hydrogen (hereinafter also referred to simply as hydrogen) with a dehydrogenation catalyst. In the dehydrogenation step, at least a part of indane is converted into indene through a dehydrogenation reaction. In the production method, since the raw material gas contains hydrogen, the dehydrogenation reaction proceeds in the presence of hydrogen.

In the raw material gas, a molar ratio of molecular hydrogen to indane (molecular hydrogen/indane) is preferably 5.0 or less, and more preferably 3.5 or less. Thus, influence of the thermodynamic equilibrium constraint is reduced, and the dehydrogenation reaction tends to more efficiently proceed. The molar ratio of molecular hydrogen to indane (molecular hydrogen/indane) is preferably 0.01 or more, and more preferably 0.05 or more. Thus, the above-mentioned effect owing to the presence of molecular hydrogen can be more remarkably attained, and indene can be obtained in a high yield.

The raw material gas may further contain an inert gas such as nitrogen or argon in addition to indane and molecular hydrogen. The raw material gas may further contain steam. Besides, the raw material gas may further contain carbon monoxide, a carbon dioxide gas, an alkane, an olefin, or the like. A total content of other components in addition to indane and molecular hydrogen may be, for example, 10.0-fold mol or less based on indane, is preferably 5.0-fold mol or less based on indane, or may be 0 (zero).

In the dehydrogenation step, for example, a reactor filled with the dehydrogenation catalyst may be used, and the dehydrogenation reaction may be performed by causing the raw material gas to pass through the reactor. As the reactor, any of various reactors used for a gas phase reaction using a solid catalyst can be used. Examples of the reactor include a fixed bed adiabatic reactor, a radial flow reactor, and a tubular reactor.

A reaction method for the dehydrogenation reaction may be, for example, a fixed bed method, a moving bed method, or a fluidized bed method. Among these, the fixed bed method is preferred from the viewpoint of equipment cost.

A temperature at which the raw material gas is contacted with the dehydrogenation catalyst (that can be said as a reaction temperature of the dehydrogenation reaction, or a temperature within the reactor) may be, from the viewpoint of reaction efficiency, 350 to 800° C., may be 400 to 700° C., or may be 450° C. to 650° C. When the reaction temperature is 350° C. or more, the yield of indene tends to be further improved because an equilibrium conversion rate of indane is not too low. When the reaction temperature is 800° C. or less, the dehydrogenation catalyst tends to retain its high activity for a longer period of time because a coke production rate is suppressed.

A pressure at which the raw material gas is contacted with the dehydrogenation catalyst (that can be said as a reaction pressure of the dehydrogenation reaction, or a pressure within the reactor) may be, for example, 0.01 to 4.0 MPa, may be 0.03 to 0.5 MPa, or may be 0.01 to 0.3 Ma. When the reaction pressure falls in the above-described range, the dehydrogenation reaction tends to easily proceed to attain further excellent reaction efficiency.

When the dehydrogenation step is performed by a continuous reaction method for continuously supplying the raw material, a mass hourly space velocity (hereinafter referred to as the "WHSV") may be 0.01 $h^{-1}$ or more, or may be 0.1 $h^{-1}$ or more. When such a WHSV is employed, the conversion rate of indane can be further increased. The WHSV may be 100 $h^{-1}$ or less, or may be 20 $h^{-1}$ or less. When such a WHSV is employed, the reactor size can be further reduced. Here, the WHSV refers to a ratio (F/W) of a supply rate (amount supplied/time) F of the raw material to the mass W of the dehydrogenation catalyst in a continuous reaction device. It is noted that further preferable ranges of amounts of the raw material and the catalyst used may be appropriately selected in accordance with the reaction conditions, the activity of the catalyst and the like, and the WHSV is not limited to the above-described range.

The production method B may further comprise a raw material synthesis step of obtaining indane by a dehydrogenation reaction of tetrahydroindene.

In such a production method, a dehydrogenation catalyst (hereinafter sometimes referred to as the first dehydrogenation catalyst) for converting tetrahydroindene into indane may be filled in an upstream stage of the reactor with the above-mentioned dehydrogenation catalyst (hereinafter sometimes referred to as the second dehydrogenation catalyst) filled in a downstream stage of the reactor. Since the above-mentioned dehydrogenation catalyst (the second dehydrogenation catalyst) is excellent in the reaction activity of the dehydrogenation reaction from indane to indene, when the upstream stage of the second dehydrogenation catalyst is filled with the first dehydrogenation catalyst, indene can be efficiently produced from tetrahydroindene.

As the first dehydrogenation catalyst, any one of solid catalysts for catalyzing a dehydrogenation reaction of tetrahydroindene can be used without any limitation. As the first dehydrogenation catalyst, for example, a chromium/$Al_2O_3$ catalyst, a platinum/$Al_2O_3$ catalyst and a Fe—K catalyst, which are used as catalysts for a dehydrogenation reaction, or a Bi—Mo catalyst usually used as a catalyst for an oxidative dehydrogenation reaction can be used.

In the production method B, a purification method employed in the purification step is not especially limited, and any method can be employed as long as the above-mentioned indene composition can be obtained.

The purification step is preferably a step of obtaining the indene composition by distillation purification of the reaction product. According to the production method B, since a hydrocarbon compound having a boiling point close to that of indene, having a condensed ring structure of a 5-membered ring and a 6-membered ring, and having 9 or 10 carbon atoms is generated as a by-product of the reaction, the above-mentioned indene composition can be easily obtained by distillation purification of the reaction product.

The preferable embodiment of the present invention has been described so far, and it is noted that the present invention is not limited to the above-described embodiment.

EXAMPLES

Now, the present invention will be described in more detail with reference to examples, and it is noted that the present invention is not limited to these examples.

Example 1

A catalyst was prepared by supporting platinum on an alumina-tin oxide support (content of tin: 23% by mass) in such a manner that an amount of platinum supported was 3.0% by mass. A tubular flow reactor filled with the catalyst was used to perform a reaction under conditions of 185° C., 0.15 MPa, and WHSV of 3.0 h$^{-1}$ with tetrahydroindene (manufactured by Tokyo Chemical Industry Co., Ltd.) used as a raw material, and thus, a reaction product containing indane was obtained.

Subsequently, a catalyst was prepared by supporting platinum and tin on a magnesia-alumina support in such a manner that amounts of platinum and tin supported were respectively 1.0% by mass and 2.7% by mass. A tubular flow reactor filled with the catalyst was used to perform a reaction under conditions of 500° C., an ordinary pressure, in the coexistence of hydrogen, and WHSV of 1.0 h$^{-1}$ with the above-described reaction product used as a raw material, and thus, a reaction product containing indene was obtained.

The thus obtained reaction product containing indene was purified by distillation to obtain an indene composition. Indene compositions respectively having an indene purity of 80% by mass, 90% by mass, 95% by mass, 98% by mass, and 99% by mass were prepared, and the composition of each of the indene compositions was analyzed by a gas chromatograph equipped with a mass spectrometer to obtain a result as shown in Table 1. A sulfur content of each indene composition was measured by an ultraviolet fluorescence method to obtain a result shown in Table 1. Besides, the respective indene compositions were visually observed to find that none of the indene compositions was colored.

Comparative Example 1

Indene derived from coal tar was measured for an indene impurity and a content of benzonitrile by gas chromatography. A sulfur content was also measured by an ultraviolet fluorescence method. Besides, it was visually checked whether or not the indene was colored. Results are shown in Table 2.

Comparative Example 2

Indene derived from coal tar and available from a different manufacturer from that of Comparative Example 1 was measured for an indene impurity and a content of benzonitrile by gas chromatography. A sulfur content was also measured by an ultraviolet fluorescence method. Besides, it was visually checked whether or not the indene was colored. Results are shown in Table 2.

TABLE 2

|  | Comparative Example 1 | Comparative Example 2 |
|---|---|---|
| Indene Purity (mass %) | 96 | 78 |
| Benzonitrile (mass %) | 2.3 | 7.7 |
| Sulfur Content (mass ppm) | 48 | 370 |
| Coloring | Pale Yellow | Pale Orange |

The invention claimed is:

1. An indene composition, comprising 80 to 99.5% by mass of indene, 0.5% by mass or less of benzonitrile, 5 ppm by mass or less of sulfur, and a non-indene component;

wherein in the non-indene component, a content ratio of a hydrocarbon compound having a condensed ring structure of a 5-membered ring and a 6-membered ring, and having 9 or 10 carbon atoms is 90% by mass or more, the hydrocarbon compound contains an alicyclic compound selected from the group consisting of bicyclo(4,3,0)-2,9-nonadiene, hexahydro-4,7-methanoindene and octahydro-4,7-methanoindene, and a content ratio of the alicyclic compound in the indene composition is 0.1 to 0.8% by mass.

TABLE 1

|  |  | Indene Purity (mass %) | | | | |
|---|---|---|---|---|---|---|
| Composition (mass %) |  | 80 | 90 | 95 | 98 | 99 |
| Indene |  | 80 | 90 | 95 | 98 | 99 |
| Alicyclic Compound | Bicyclo(4,3,0)-2,9-nonadiene | 0.28 | 0.32 | 0.33 | 0.34 | 0.34 |
|  | Hexahydro-4,7-methanoindene | 0.14 | 0.16 | 0.17 | 0.18 | 0.18 |
|  | Octahydro-4,7-methanoindene | 0.19 | 0.21 | 0.22 | 0.23 | 0.23 |
| Aromatic Compound | Indane | 18.66 | 8.49 | 3.41 | 0.36 | 0.25 |
|  | Methylindane | 0.27 | 0.31 | 0.33 | 0.34 | 0.00 |
|  | Methylindene | 0.32 | 0.36 | 0.37 | 0.39 | 0.00 |
| Benzonitrile (mass %) |  | 0 | 0 | 0 | 0 | 0 |
| Sulfur Content (mass ppm) |  | <1 ppm | <1 ppm | <1 ppm | <1 ppm | <1 ppm |
| Coloring |  | not colored | not colored | not colored | not colored | not colored |

2. The indene composition according to claim 1, wherein the hydrocarbon compound contains at least one aromatic compound selected from the group consisting of indane, methylindane, and methylindene.

3. The indene composition according to claim 2, wherein a content of the aromatic compound is 0.1 to 19.9% by mass.

* * * * *